United States Patent [19]

Beautement et al.

[11] Patent Number: 4,937,374
[45] Date of Patent: Jun. 26, 1990

[54] PROCESS FOR PREPARING METHYL 3-METHOXY-2-(2-PHENOXYPHENYL)-PROPENOALIS

[75] Inventors: Kevin Beautement, Wokingham; John M. Clough, Marlow Buckinghamshire; Christopher R. A. Godfrey, Bracknell, all of England

[73] Assignee: Imperial Chemical Industries PLC, London, England

[21] Appl. No.: 242,679

[22] Filed: Sep. 9, 1988

[30] Foreign Application Priority Data

Sep. 9, 1987 [GB] United Kingdom ............ 8721221
Sep. 24, 1987 [GB] United Kingdom ............ 8722537
Feb. 25, 1988 [GB] United Kingdom ............ 8804433

[51] Int. Cl.$^5$ ............................................. C07C 69/76
[52] U.S. Cl. ................................................. 560/060
[58] Field of Search ......................................... 560/060

[56] References Cited

U.S. PATENT DOCUMENTS

4,709,078 11/1987 Schirmer et al. ............... 560/60

FOREIGN PATENT DOCUMENTS

57047   1/1981 European Pat. Off. .
0178826 4/1986 European Pat. Off. ......... 560/60
2117826 4/1970 Fed. Rep. of Germany .
7075947 10/1980 Japan .
7075948 10/1980 Japan .
2078743 1/1982 United Kingdom .

OTHER PUBLICATIONS

Chemical Abstracts, 77 (1972) 100667f and 79, (1973) 115261j.
Fanta, *Chem. Reviews*, 38:139 (1946) and 64:613 (1964).

*Primary Examiner*—Paul J. Killos
*Attorney, Agent, or Firm*—Cushman, Darby & Cushman

[57] ABSTRACT

Process for the preparation of a compound of general formula (I):

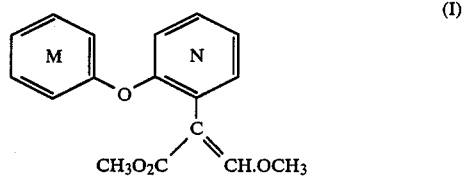

by reacting a compound of general formula (II)

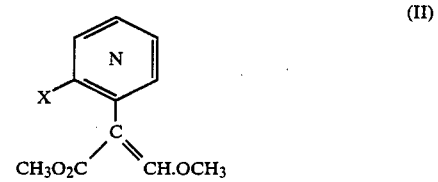

(X is halide; rings M and N are optionally substituted) with an optionally substituted phenol in the presence of a base, or with an optionally substituted phenolate salt; preferably in the presence of a catalyst which is a transition metal, a transition metal salt or compound or a mixture thereof.

4 Claims, No Drawings

PROCESS FOR PREPARING METHYL 3-METHOXY-2-(2-PHENOXYPHENYL)-PROPENOALIS

This invention relates to a process for the preparation of derivatives of propenoic acid which are useful as fungicides or as chemical intermediates in the preparation of fungicides.

According to the invention, there is provided a process for the preparation of a compound of general formula (I):

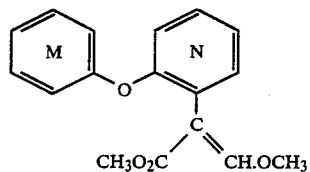

(I)

wherein the benzene rings M and N optionally carry one or more substituents which are not reactive under the conditions of the process, which comprises reacting a compound of general formula (II):

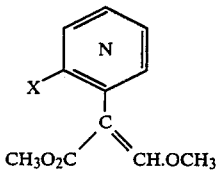

(II)

wherein X is halogen (preferably iodine, chlorine or bromine) with a phenol of general formula (III):

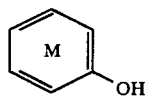

(III)

in the presence of a base, or with a salt of the phenol (III), preferably in the presence of a catalyst which comprises a suitable transition metal, a transition metal salt or compound or a mixture thereof.

In this process, compounds of general formula (I) can be obtained by reaction of compounds (II) with salts derived from phenols of general formula (III) by prior treatment of the phenols with base. In this aspect of the invention, the additional presence of a base during the coupling reaction is not required.

A solvent may be employed in carrying out the process of the invention. Suitable solvents are those in which both compounds (II) and (III) (or salts derived therefrom) are soluble or practically soluble and which do not react with either of these substrates under the conditions of the reaction. Solvents which may be used include dipolar aprotic solvents such as N,N-dimethylformamide, dimethylsulphoxide, N,N-dimethylacetamide and methyl isobutyl ketone. In certain cases, when either of the substrates is a liquid under the conditions of the reaction, it is possible to perform the reaction in the absence of an added solvent.

Suitable bases for use in the process are those which act either by abstraction of the phenolic proton of compound (iii) prior to reaction with substrate (II) or by neutralisation of any acid produced during the reaction, without reacting significantly with substrate (II) or product (I). An example of such a base is anhydrous potassium carbonate.

Suitable transition metals or transition metal salts or compounds which may catalyse the process include copper metal, copper salts and compounds and nickel salts and compounds, such as copper bronze and copper(I) chloride, which may be used separately or in admixture (see, for example, A. A. Moroz and M. S. Shvartsberg, *Russian Chemial Reviews*, 1974, 43 (8), 679–689).

The process may be conducted over a wide range of temperatures. In practice, the temperature will be chosen so that reaction occurs at a reasonable and convenient rate. This will usually be in the range 100° C. to 200° C. depending on the reactivity of the substrates (II) and (III) and the nature of the catalyst.

The presence of the propenoate double bond gives rise to geometric isomers of the compounds (I) and (II). These isomers are denoted by the commonly used terms (E) and (Z) according to the Cahn-Ingold-Prelog system which is fully described in the literature (see, for example, J. March, "Advanced Organic Chemistry", 3rd Edition, Wiley-Interscience, page 109 et seq). Either the (E)- or the (Z)-isomer of compounds of general formula (II) or mixtures thereof can be used as substrates in the process of the invention. Under the conditions of the reaction, the (Z)-isomer of compounds of general formula (II) usually undergoes stereomutation to the corresponding (E)-isomer, reaction then proceding to give compounds of general formula (I) of (E)-geometry. That is, compounds of formula (I) of (E)-geometry are usually formed irrespective of the geometry of the precursors of formula (II).

The process of the invention is of special interest in the preparation of fungicidal compounds; for instance, those described in EP-A-0178826 and, in particular, those compounds of general formula (IV)

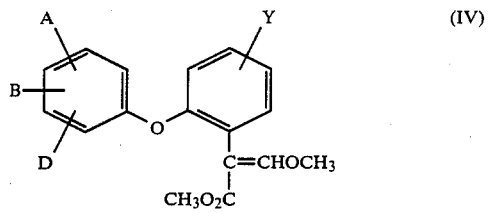

(IV)

wherein A, B, D and Y, which may be the same or different, are hydrogen or halogen atoms, or optionally substituted alkyl, optionally substituted alkenyl, optionally substituted aryl, optionally substituted heteroaryl, optionally substituted alkynyl, optionally substituted alkoxy, optionally substituted aryloxy, optionally substituted heteroaryloxy, optionally substituted arylalkoxy, optionally substituted acyloxy, optionally substituted sulphonyloxy, optionally substituted amino, optionally substituted arylazo, acylamino, nitro, cyano, —$CO_2R^1$, —$CONR^2R^3$, —$COR^4$, —$CR^5$=$NR^6$, or —N=$CR^7R^8$ groups, or the groups A and B, when they are in adjacent positions on the phenyl ring, may joint to form a fused ring, optionally containing one or more heteroatoms; and $R^1$, $R^2$, $R^3$, $R^4$, $R^5$, $R^6$, $R^7$ and $R^8$, which may be the same or different, are hydrogen atoms or alkyl, cycloalkyl, alkenyl, alkynyl, optionally substituted aryl, optionally substituted heteroaryl, optionally substituted aralkyl, or cycloalkylalkyl groups.

The process may also be used to prepare chemical intermediates useful in the preparation of fungicides.

The substrate of general formula (II) may be prepared according to processes outlined in EP-A-0178826.

Compounds of general formula (III) can be prepared by known methods as described in the chemical literature.

The following examples illustrate the invention. Throughout these examples, reactions involving water-sensitive intermediates were performed under a nitrogen atmosphere in dry solvents, the term 'ether' refers to diethyl ether, magnesium sulphate was used to dry solutions, solutions were concentrated under reduced pressure, and chromatography was performed on columns of silica gel. Unless otherwise stated, n.m.r spectra were recorded at 270 MHz using deuteriochloroform solutions and tetramethylsilane as the internal standard. Where shown, spectroscopic data are selective; no attempt is made to list every absorption in all cases.

The following abbreviations are used:
IR = infrared
n.m.r = nuclear magnetic resonance
MS = mass spectroscopy
GC = gas chromatography
s = singlet
d = doublet
t = triplet
m = multiplet
br = broad
m.p = melting point
p.p.m = parts per million
DMF = N,N-dimethylformamide

EXAMPLE 1

This Example illustrates the synthesis of (E)-methyl 3-methoxy-2-[2-(3-methylphenoxy)phenyl]propenoate.

A solution of ortho-bromophenylacetic acid (5.14 g) in dry methanol (40 ml) containing 5 drops of concentrated sulphuric acid was heated at reflux for three hours. The reaction mixture was cooled, then poured into iced water (150 ml) and extracted (2×75 ml) with ether. The ether layers were combined, washed successively with water (×3), saturated sodium bicarbonate solution (×2), water (×1) and saturated brine and then dried. Filtration and evaporation gave methyl ortho-bromophenylacetate (5.23 g, 96%) as a pale yellow liquid, IR maximum 1742 cm$^{-1}$, which was used without further purification.

A mixture of methyl ortho-bromophenylacetate (5.23 g) and methyl formate (27.46 g) in DMF(6 ml) was added dropwise to a stirred suspension of sodium hydride (1.10 g) in DMF (45 ml) at 0° to 5° C. (frothing). When thin-layer chromatography showed that reaction was complete, the mixture was poured into water, acidified and extracted with ether. The extracts were dried and concentrated to give crude methyl 2-(2-bromophenyl)-3-hydroxypropenoate (5.95 g) as a yellow liquid which was used directly in the next step. The crude methyl 2-(2-bromophenyl)-3-hydroxypropenoate (5.95 g) was stirred with anhydrous potassium carbonate (6.38 g) and dimethyl sulphate (2.75 g) in DMF (40 ml). After 3 hours at room temperature, the reaction mixture was poured into water and extracted with ether (2×75 ml). The combined ether layers were washed with water and brine (×1) and dried. Filtration and evaporation gave a yellow oil which crystallised on standing to give (E)-methyl 2-(2-bromophenyl)-3-methoxypropenoate (5.20 g, 88% yield from methyl ortho-bromophenylacetate) as a crystalline solid, m.p. 68°–69° C., IR maxima 1712, 1638 cm$^{-1}$; $^1$H n.m.r delta 3.73 (3H, s); 3.86 (3H, s); 7.56 (1H, s) p.p.m.

Potassium carbonate (260 mg), (E)-methyl 2-(2-bromophenyl)-3-methoxypropenoate (250 mg) and copper(I) chloride (catalytic) were added successively to 3-methylphenol (210 mg). The resulting mixture was heated with stirring at 170° C. for 3.5 hours then allowed to cool. The mixture was taken up in DMF (3 ml), then poured into water, acidified with dilute hydrochloric acid, then extracted with ether (3×25 ml). The combined extracts were washed thoroughly with aqueous sodium hydroxide (×3), then with water (×2) and brine, then dried. The resulting solution was concentrated and chromatographed (eluant 30% ether in petrol) to give the title compound (120 mg, 42% yield) as a white crystalline solid, m.p. 79°–80° C., IR maxima 1711, 1632 cm$^{-1}$; $^1$H n.m.r. delta 2.30 (3H, s), 3.62 (3H, s), 3.77 (3H, s), 7.48 (1H, s) p.p.m.

EXAMPLE 2

This Example illustrates the synthesis of (E)-methyl 2-[2-(3-chlorophenoxy)phenyl]-3-methoxypropenoate.

Sodium (66 mg) was dissolved in dry methanol (2 ml) under nitrogen. 3-Chlorophenol (372 mg) was added in one portion to give a yellow solution which was stirred at room temperature for 45 minutes. The methanol was evaporated off to give a yellow oil and (E)-methyl 2-(2-bromophenyl)-3-methoxypropenoate (300 mg, prepared as described in Example 1) and a catalytic quantity of copper bronze were added. The resulting mixture was heated at 150° C. for 2 hours and at 170° C. for 2 hours. A catalytic quantity of copper(I) chloride was added and heating at 150° C. was continued for a further 2 hours. Analysis of the reaction mixture at this stage by GC/MS indicated that it was composed of unreacted (E)-methyl 2-(2-bromophenyl)-3-methoxypropenoate (37%), 3-(3-chlorophenoxy)phenol (15%) and *the title compound* (26%), together with several minor components (none greater than 5% of the mixture).

EXAMPLE 3

This Example illustrates an alternative synthesis of (E)-methyl 3-methoxy-2-[2-(3-methylphenoxy)phenyl]-propenoate.

A mixture of methyl ortho-bromophenylacetate (4.10 g, prepared as described in Example 1) and selenium dioxide (4.92 g) was stirred for 25 hours at 190° C. After cooling, the mixture was diluted with dichloromethane (100 ml) then filtered through 'Supercel'. The filtrate was washed successively with saturated aqueous sodium bicarbonate (×2) and brine, then dried and concentrated to give a yellow liquid (3.60 g) containing (52% by GC-MS) methyl (2-bromobenzoyl)formate and unreacted methyl ortho-bromophenylacetate.

Potassium tert-butoxide (2.33 g) was added to a vigorously-stirred suspension of (methoxymethyl)triphenylphosphonium chloride (7.90 g) in ether (80 ml) at room temperature. After 15 minutes, a solution of the crude methyl (2-bromobenzoyl)formate (3.60 g) in ether (10 ml) was added in a single portion. After a further 15 minutes, the reaction mixture was poured into water (150 ml), the aqueous and organic layers were separated, and the former was extracted with a further portion of ether (100 ml). The combined ether layers were washed successively with water (×2) and brine, then dried and concentrated to give a yellow oil (5.81 g) containing, in a ratio of about 6:5, the (E)- and (Z)-isomers respectively of methyl 2-(2-bromophenyl)-3-methoxypropenoate. Chromatography using ether:hexane (1:1) as eluant allowed the pure (Z)-isomer (0.450 g) to be isolated as a pale yellow oil, IR (film) 1712, 1638 cm$^{-1}$, $^1$H n.m.r delta 3.71 (3H, s), 3.95 (3H, s), 6.57 (1H, s) p.p.m.

A mixture of (Z)-methyl 2-(2-bromophenyl)-3-methoxypropenoate (0.370 g), 3-methylphenol (0.294 g), potassium carbonate (0.377 g) and copper(I) chloride (catalytic) was heated at 170° C. After 45 minutes, analysis of the mixture by GC and thin-layer chromatography showed that it contained roughly equal amounts of (E)-methyl 2-(2-bromophenyl)-3-methoxypropenoate and the title compound, and none of the original (Z)-methyl 2-(2-bromophenyl)-3-methoxypropenoate could be detected. After a further 3¼ hours, the reaction mixture was allowed to cool; it was dissolved in DMF (5 ml) then diluted with water, acidified with dilute hydrochloric acid and extracted with ether. These extracts were washed successively with aqueous sodium hydroxide (×3), water (×2) and brine, then dried, concentrated and chromatographed using ether:hexane (1:1) as eluant to give the title compound (0.110 g, 27% yield) as an off-white solid whose spectroscopic data were the same as those for the title compound of Example 1.

EXAMPLE 4

This Example illustrates the preparation of (E)-methyl 3-methoxy-2-[2-(3-[4-phenoxyphenoxy]phenoxy)phenyl]propenoate.

A mixture of 3-(4-phenoxyphenoxy)phenol (4.11 g), (E)-methyl 2-(2-bromophenyl)-3-methoxypropenoate (2.0 g, prepared as described in Example 1), potassium carbonate (2.04 g) and copper (I) chloride (0.1 g) was stirred at 170°–180° C. for 4 hours then allowed to cool. The mixture was diluted with water and extracted with ether. The ether extracts were washed successively with aqueous sodium hydroxide and brine then dried and concentrated to give a brown gum (4.47 g). This gum was chromatographed using varying proportions (up to 20%) of ether in hexane as eluant to give the title compound (2.06 g, 60%) as an amber-coloured gum.

$^1$H n.m.r. (90 MHz) delta: 3.62 (3H, s), 3.77 (3H, s), 6.64–7.49 (17H, m), 7.50 (1H, s) ppm.

EXAMPLE 5

This Example illustrates the preparation of (E)-methyl 3-methoxy-2-[2-(3-[3-nitrophenoxy]phenoxy)phenyl]propenoate.

A mixture of 3-(3-nitrophenoxy)phenol (1.7 g), (E)-methyl 2-(2-bromophenyl)-3-methoxypropenoate (2.0 g, prepared as described in Example 1), potassium carbonate (1.0 g) and copper (I) chloride (1.0 g) was stirred at 170°–180° C. for 5 hours then allowed to cool. The mixture was diluted with water and extracted with ether. The extracts were washed successively with aqueous sodium hydroxide and brine, then dried and concentrated to give a brown oil (3.12 g). Chromatography using varying proportions (up to 20%) of ether in hexane as eluant gave the title compound (1.06 g, 34% yield) as a yellow oil.

$^1$H n.m.r. (270 MHz) delta: 3.60 (3H, s), 3.76 (3H, s), 6.66–6.83 (3H, m), 7.02 (1H, d), 7.18 (1H, d), 7.22–7.38 (3H, m), 7.45–7.52 (1H, m), 7.49 (1H, s), 7.78 (1H, m), 7.92–7.97 (1H, m) ppm.

We claim:

1. A process for the preparation of a compound of general formula (I):

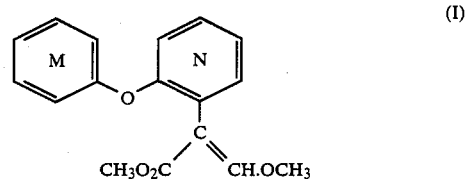

wherein the benzene rings M and N optionally carry one or more substituents which are not reactive under the conditions of the process, which comprises reacting a compound of general formula (II):

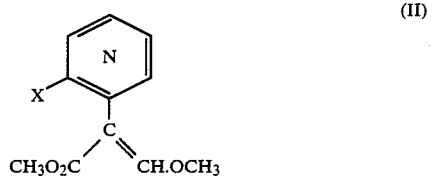

wherein X is a halogen with a phenol of general formula (III):

in the presence of a base, or with a salt of the phenol (III); preferably in the presence of a catalyst which comprises a suitable transition metal, a transition metal salt or compound or a mixture thereof.

2. A process according to claim 1 in which is present a catalytic amount of copper metal or a copper salt or compound or a mixture thereof.

3. A process according to claim 1 or 2 which is carried out at a temperature of from 100° C. to 200° C.

4. A process according to claim 1 or claim 2 in which the base is anhydrous potassium carbonate.

* * * * *